(12) United States Patent
Potts

(10) Patent No.: US 6,598,456 B2
(45) Date of Patent: Jul. 29, 2003

(54) METHOD AND SYSTEMS FOR CONTROL OF ACCELERATION PULSES GENERATED BY HYGE TYPE CRASH SIMULATION SLEDS

(76) Inventor: Gerald R. Potts, 3422 Bancroft Rd., Fairlawn, OH (US) 44333

(\*) Notice: Subject to any disclaimer, the term of this patent is extended or adjusted under 35 U.S.C. 154(b) by 0 days.

(21) Appl. No.: 09/944,827

(22) Filed: Aug. 31, 2001

(65) Prior Publication Data

US 2002/0026820 A1 Mar. 7, 2002

Related U.S. Application Data

(60) Provisional application No. 60/229,558, filed on Sep. 1, 2000.

(51) Int. Cl.$^7$ .................................................. G01N 3/30
(52) U.S. Cl. ..................................... 73/12.07; 73/865.3
(58) Field of Search .......................... 73/865.3, 862, 73/1.01, 12.04, 12.07

(56) References Cited

U.S. PATENT DOCUMENTS 3,739,625 A * 6/1973 Roberts et al. ................ 73/12
4,648,490 A * 3/1987 Bergloff ..................... 188/297
5,245,856 A * 9/1993 Pazzaglia et al. ................ 73/9
5,483,845 A * 1/1996 Stein et al. ................. 73/865.3
5,485,758 A * 1/1996 Brown et al.
5,929,348 A * 7/1999 Stein et al. ................. 73/865.3

OTHER PUBLICATIONS

Stein et al., U.S. patent application 2002/0121144 A1, Sep. 5, 2002.*

\* cited by examiner

Primary Examiner—Helen Kwok
Assistant Examiner—C D Garber
(74) Attorney, Agent, or Firm—Roetzel & Andress

(57) ABSTRACT

An acceleration pulse modulation method for HYGE (Hydraulically Controlled, Gas Energized) crash simulation sleds uses servo-controlled accelerators on moveable parts of the crash simulator components and acceleration measurement instrumentation for comparison of measure acceleration of the sled with a desired acceleration to enable dynamic adjustment of the total accelerating force applied to the sled via servo-controlled accelerators, based upon measured acceleration error in order to eliminate acceleration error.

8 Claims, 2 Drawing Sheets

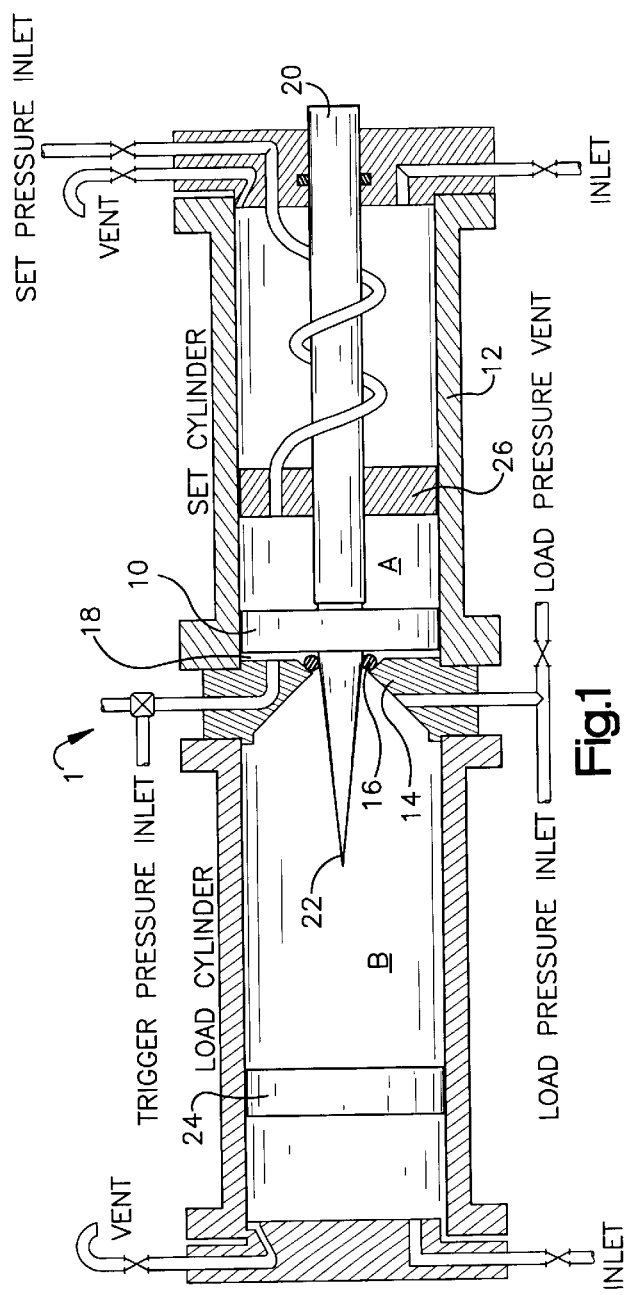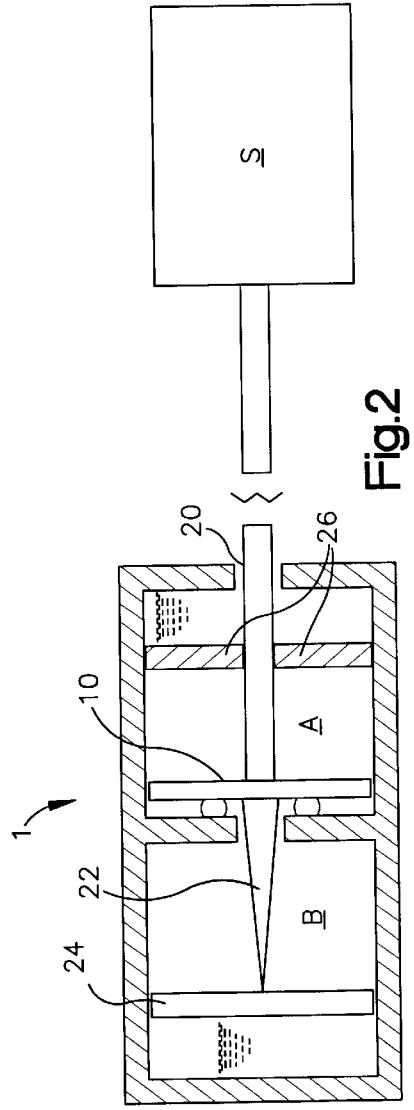

METHOD AND SYSTEMS FOR CONTROL OF ACCELERATION PULSES GENERATED BY HYGE TYPE CRASH SIMULATION SLEDS

This application claims benefit of provisional application Ser. No. 60/229,558, filed Sep. 1, 2000.

FIELD OF THE INVENTION

The present invention pertains generally to the control of the acceleration pulse delivered by HYGE (Hydraulically Controlled, Gas Energized) crash simulation sleds used in safety testing of vehicle components.

BACKGROUND OF THE INVENTION

The HYGE (Hydraulically Controlled, Gas Energized) system derives its powerful thrust force from an actuator assembly 1 which uses differential gas pressure acting on the two faces of a thrust piston 10 in a closed cylinder 12, as shown in FIG. 1. The cylinder is separated into two chambers A, B by an orifice plate 14. A relatively low gas pressure in chamber A, known as the Set Cylinder, forces the thrust piston 10 against a seal ring 16 on the orifice plate 17. The area of the entire thrust piston face is exposed to the gas pressure in chamber A, defined by floating pistons 26 opposed to thrust piston 10. On the other side of the piston, only the small area within the seal is exposed, through the orifice opening, to the gas pressure in chamber B, known as the Load Cylinder, in which a floating piston 24 is located.

In preparation for firing, compressed gas is introduced into the Load Cylinder until the forces on the thrust piston 10 are equalized. To fire the piston, a small burst of compressed gas is introduced into the trigger chamber 18, which is the small area within the seal on the chamber B side of the piston. This burst upsets the equilibrium, opening the seal at the orifice plate 17 and exposing the entire surface area of the piston to the the seal at the orifice plate 17 and exposing the entire surface area of the piston to the higher pressure in the Load Cylinder. This results in a powerful thrust force being applied to the thrust piston in the direction of chamber A. This thrust force is then transmitted to a crash sled through the thrust column 20.

The thrust force has, until now, been controlled by regulating the compressed gas flow through the orifice plate by the shape of the metering pin 22, which is progressively drawn through the orifice as the metering pin, thrust piston, and thrust column assembly move in the direction of chamber A during the firing event.

The HYGE (Hydraulically Controlled, Gas Energized) reaction simulates the longitudinal deceleration conditions of an impact, but in reverse. Prior to an actual crash, the test vehicle and test dummies each move at a constant velocity. At impact, they are stopped very rapidly. During a HYGE (Hydraulically Controlled, Gas Energized) crash simulation sled test, the test vehicle and dummies, which are attached to the sled, are initially at zero velocity. This situation simulates the constant velocity condition prior to an actual crash. The metering pin programmed acceleration of the HYGE (Hydraulically Controlled, Gas Energized) sled drives an automobile assembly attached to the crash sled, which is shown in FIG. 2, out from under the test dummies, producing a response similar to that caused by the rapid deceleration of a moving vehicle. The acceleration and deceleration effects are interchangeable because the acceleration—time relationships are the same in both cases.

The metering pin controlled force output works well, but is cumbersome and time-consuming to change to another force—time profile, requiring disassembly of the Set and Load Cylinders and removal and insertion of a different-shaped metering pin. A large inventory of such metering pins may be required in order to represent all the force—time shapes required.

SUMMARY OF THE INVENTION

Control of the force—time relationship during actuator motion is possible by other means than just metering pin shape. Instead of allowing all the force applied to the thrust piston to be directly applied to the thrust column and then used to accelerate the sled, an electronically controlled force control device may be employed to control the amount of force being made available to accelerate the sled.

Such an acceleration control (accelerator) device may take the form of a brake or force actuator acting in parallel with the HYGE (Hydraulically Controlled, Gas Energized) actuator to provide a force-path to ground either in parallel with the sled, or a force generator/absorber in parallel with the HYGE (Hydraulically Controlled, Gas Energized) actuator. This parallel accelerator device is to be closed-loop controlled using sled acceleration as the feedback signal source to compare with the desired acceleration value at a sequence of time increments and to apply a corresponding acceleration output to the sled or HYGE (Hydraulically Controlled, Gas Energized) actuator to drive the acceleration error (difference between desired and actual acceleration) toward zero, thus achieving true closed-loop control over the acceleration—time pulse during the actuator firing event.

BRIEF DESCRIPTION OF THE FIGURES

FIG. 1 is a cross-sectional drawing of an exemplary HYGE (Hydraulically Controlled, Gas Energized) actuator.

FIG. 2 is an operational schematic of such a HYGE (Hydraulically Controlled, Gas Energized) actuator as applied to a crash simulation sled with the thrust column being used to accelerate the sled in a reverse crash situation.

DETAILED DESCRIPTION OF PREFERRED AND ALTERNATE EMBODIMENTS

The accelerator may be composed of servo-controlled brakes (indicated generally at 45 in FIG. 4) to rapidly vary the total force applied to the sled, or an active actuator to rapidly apply either additional accelerating or retarding force to the sled in a dynamically varying and controlled manner, which variation shall depend upon the acceleration being sensed by a sled-mounted accelerometer then being subtracted from the desired acceleration value with the difference (error value) being used to control the application of sled acceleration that is appropriate to decrease the acceleration error. Such an accelerator may be applied to the thrust column as it extends from the actuator during firing, to a specially contoured metering pin inside of Chamber B, to the sled via a its braking system, to the sled via a set of auxiliary brakes or active actuator(s), or to the sled via disk brake controlled cable-reel winch(es) attached to the HYGE (Hydraulically Controlled, Gas Energized) actuator case (or foundation) with the winch cables attached either to the thrust column or to the sled itself.

Figure 3A:
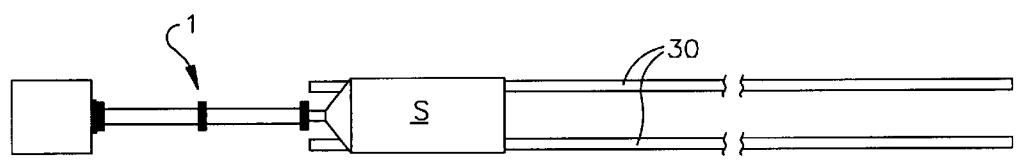
FIG. 3 shows top and side views of a typical HYGE (Hydraulically Controlled, Gas Energized) sled arrangement with which the invention is used.
Figure 3B:
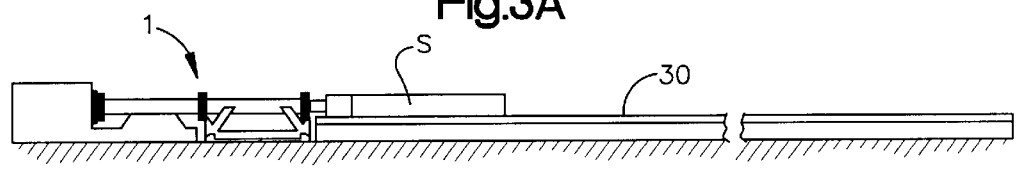

A preferred embodiment is to attach linear braking rails 30 to the sleds and apply brakes 45 to these rails with the brake actuators being attached to the existing sled support rails, rail foundations and/or the HYGE (Hydraulically Controlled, Gas Energized) actuator to react the force being generated by the brakes and, in turn, being applied to the sled or actuator thrust column, as shown for example in FIG. 3.

Figure 4:
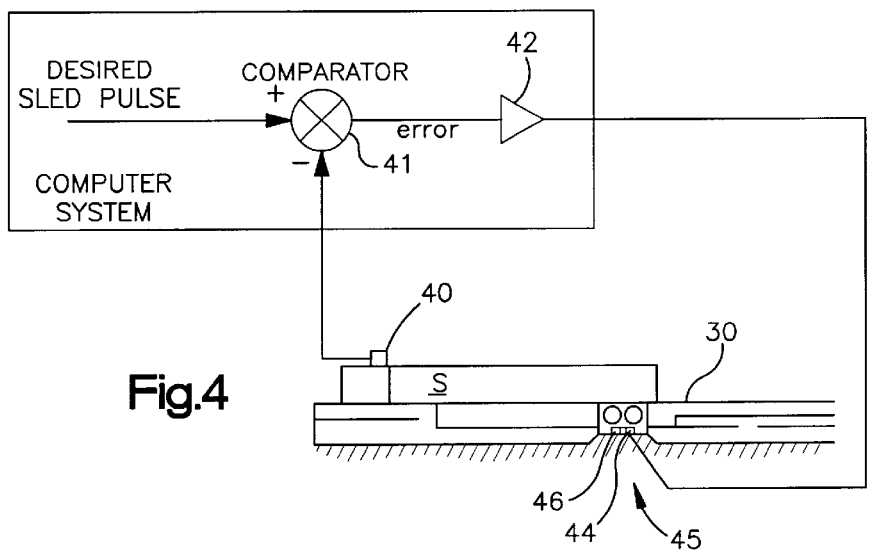
FIG. 4 is a schematic showing closed-loop acceleration control of the crash simulation sled.

FIG 4. schematically represents a device which performs the computerized closed-loop acceleration control including the storage, recall, and comparison of the desired acceleration pulse shape with the acceleration pulse that is either currently being generated during an actuator firing event, or has previously been generated and recorded for analysis. The difference between the desired acceleration and actual acceleration, as measured by accelerometer 40 and compared by a comparator 41, is then recorded as an error and is output, as shown in FIG 4., to a servo amplifier 42 for conversion into a driving signal to control a servo valve (controller) 44 that, in turn, controls the accelerator(s) 46 force being applied to either the sled, as shown, or to the HYGE (Hydraulically Controlled, Gas Energized) actuator thrust column or metering pin. As shown if FIG 4, the brake rail is attached to the sled and the actuator is attached to the sled rails, rail foundations, and/or HYGE (Hydraulically Controlled, Gas Energized) actuator to provide a path to ground for the absorbed force. The control signal thus applied is varied in order to either immediately decrease the error signal toward zero error (if real-time control is being used) or to decrease the error signal on a subsequent firing if post-firing review and corrections are employed. A computer employing digital PID (proportional, integrative, derivative) control algorithms is ideal for this purpose, but analog circuitry may serve also.

Figure 5:
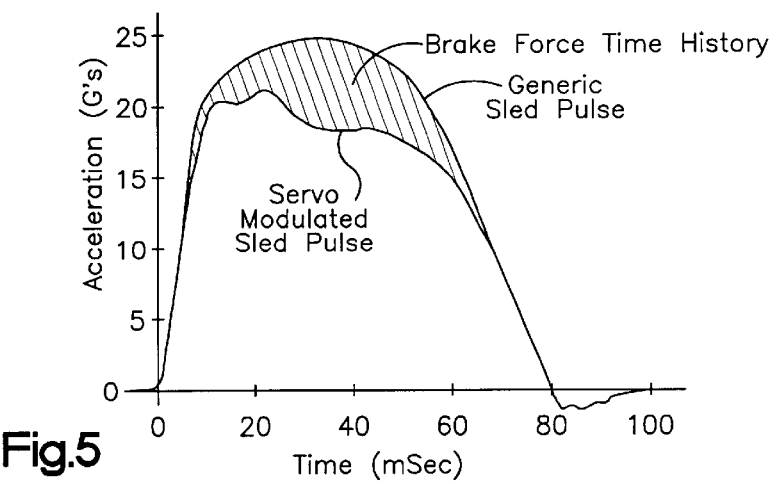
FIG. 5 is a graph of a HYGE (Hydraulically Controlled, Gas Energized) acceleration—time history (acceleration pulse) available with a generic metering pin and an example pulse shape after controlled accelerator modulation using the methods and systems of the invention.

In addition to the servo-controlled accelerators, the HYGE (Hydraulically Controlled, Gas Energized) metering pin 22 is preferably either removed altogether, or replaced with a generic metering pin to create a generic sled pulse, which the accelerator will modulate into the desired shape, as shown in FIG. 5, where the cross-hatched area between the generic sled pulse and the servo modulated sled pulse representing the acceleration force being applied by a braking mechanism, in this instance.

The servo-controlled acceleration system of the present invention provides the first active control capability to be applied to HYGE (Hydraulically Controlled, Gas Energized) sleds and allows computerized electronic control of the acceleration—time sled pulse from stored histories of such tests for later duplication without requiring replacement of the metering pin for each new acceleration pulse shape.

The invention claimed is:

1. A method of acceleration pulse modulation for a hydraulically controlled, gas energized crash simulation sled by:

attaching one or more servo-controlled accelerators to moveable parts of a hydraulically controlled, gas energized actuator or crash simulator sled;

installing a generic pulse shaping metering pin or total removal of the metering pin; and measuring the acceleration of said sled, then comparing the measured acceleration of the sled with the desired acceleration either at any instant in time during the sled launch or following the launch and dynamically adjusting the total accelerating force applied to the sled via the one or more servo-controlled accelerators, such adjustment to be based upon the acceleration error found during the comparison of sled acceleration with the desired acceleration.

2. The method of claim 1 wherein the one or more servo-controlled accelerators are each comprised of one or more existing sled brakes with a servo-controlled hydraulic valve, a pressurized hydraulic fluid source, and a tank reservoir to receive spent-pressure hydraulic fluid being removed from the braking system by the servo valve.

3. The method of claim 1 wherein the one or more servo-controlled accelerators are each comprised of one or more thrust column brakes with a servo-controlled hydraulic valve, a pressurized hydraulic fluid source, and a tank reservoir to receive spent-pressure hydraulic fluid being removed from the braking system by the servo valve.

4. The method of claim 1 wherein the one or more servo-controlled accelerators are each comprised of one or more metering pin brakes with a servo-controlled hydraulic valve, a pressurized hydraulic fluid source, and a tank reservoir to receive spent-pressure hydraulic fluid being removed from the braking system by the servo valve.

5. The method of claim 1 wherein the one or more servo-controlled accelerators are each comprised of at least one brake with a servo-controlled hydraulic valve, a pressurized hydraulic fluid source, and a tank reservoir to receive spent-pressure hydraulic fluid removed from the braking system by the servo valve.

6. The method of claim 1 wherein the one or more servo-controlled accelerators are each comprised of a hydraulic actuator with a servo-controlled hydraulic valve, a pressurized hydraulic fluid source, and a tank reservoir to receive spent-pressure hydraulic fluid removed from the hydraulic actuator by the servo valve.

7. The method of claim 1 wherein the one or more servo-controlled accelerators are each comprised of a rotary hydraulic actuator applying torque to a pinion gear meshing with a rack attached to either the sled or an extension of a thrust column with a servo-controlled hydraulic valve, a pressurized hydraulic fluid source, and a tank reservoir to receive spent-pressure hydraulic fluid being removed from the rotary hydraulic actuator by the servo valve.

8. The method of claim 1 wherein the one or more servo-controlled accelerators are each comprised of one or more disk braked cable winches attached to the hydraulically controlled, gas energized actuator with the cables attached either to a thrust column or to the crash simulation sled with one or more servo-controlled hydraulic valves, a pressurized hydraulic fluid source, and a tank reservoir to receive spent-pressure hydraulic fluid being removed from a braking system by the servo valve, modulating said disk brakes to vary sled acceleration.

* * * * *